US005700590A

United States Patent [19]

Masor et al.

[11] Patent Number: 5,700,590
[45] Date of Patent: Dec. 23, 1997

[54] NUTRITIONAL FORMULA WITH RIBO-NUCLEOTIDES

[75] Inventors: Marc Leif Masor, Worthington; James Lee Leach, Columbus; Bruce Edward Molitor, Westerville; John Durand Benson, Powell; Jeffrey H. Baxter, Galena, all of Ohio

[73] Assignee: Abbott Laboratories, Abbott Park, Ill.

[21] Appl. No.: 585,221

[22] Filed: Jan. 11, 1996

Related U.S. Application Data

[63] Continuation-in-part of Ser. No. 178,687, Jan. 10, 1994, Pat. No. 5,492,899.
[51] Int. Cl.$^6$ .................. A23L 1/305; A61K 31/70
[52] U.S. Cl. .................. 426/656; 426/69; 426/72; 426/73; 426/541; 426/601; 426/658; 426/801; 514/47; 514/45; 514/46; 514/50; 514/51
[58] Field of Search .................. 426/541, 801, 426/69, 72, 73, 658, 656, 601; 514/47, 45, 46, 49, 50, 51

[56] References Cited

U.S. PATENT DOCUMENTS

| | | |
|---|---|---|
| 3,231,385 | 1/1966 | Ziro et al. |
| 4,544,559 | 10/1985 | Gil et al. |
| 4,758,553 | 7/1988 | Ogoshi . |
| 4,994,442 | 2/1991 | Gil et al. |
| 5,021,245 | 6/1991 | Borschel et al. |
| 5,066,500 | 11/1991 | Gill et al. |
| 5,075,225 | 12/1991 | Wong et al. |
| 5,221,545 | 6/1993 | Borschel et al. |
| 5,223,285 | 6/1993 | DeMichele et al. |
| 5,268,365 | 12/1993 | Rudloph et al. |
| 5,492,899 | 2/1996 | Masor et al. .................. 426/73 |

FOREIGN PATENT DOCUMENTS

| | | |
|---|---|---|
| 1709692 | 7/1992 | Australia . |
| 302807 | 5/1988 | European Pat. Off. . |
| 375408 | 12/1989 | European Pat. Off. . |
| 2 152 814 | 12/1984 | United Kingdom . |
| 2 216 416 | 3/1989 | United Kingdom . |

OTHER PUBLICATIONS

Janas, et al., "The Nucleotide Profile of Human Milk," Pediatric Research, 16:659–662 (1992).

Gil, et al., "Acid–Soluble Nucleotides of Human Milk at Different Stages of Lactation," Journal of Dairy Research, 49:301–307 (1992).

Leach, et al., "Nucleic Acid Content of Enteral Formulas," Fed. Soc. Exp., Biology, Abstract #2184, p. A378 (1993).

Espinoza, et al., "Nucleotice–Enriched Milk and Diarrheal Disease in Infants" Fed. Soc. Exp. Biology, Abstract #16, p. 739 (1993).

Zhang, et al., "Immunomodulatory Actions of Nucleotides on Ab/Ig Production by Murine Spleen Lymphocytes in Vivo and In Vitro," Fed. Soc. Exp. Biology, Abstract #2389, p. A413 (1993).

Brunser, et al., "Effect of Dietary Nucleotide Supplementation on Diarrhoeal Disease in Infants," Acta Paediatr, 83:188–191 (1994).

Rudolph, et al., "Role of RNA as a Dietary Source of Pyrimidines and Purines in Immune Function," Nutrition, 6:45–52 (1990).

Rudolph, et al., "Nucleotides" Micronutrient Building Blocks of Nutrition, Nutrition, Sep. 1989, pp. 8–13.

Oski, et al., "The Evolution of Infant Formula," Nutrition, Sep. 1989, pp. 4–7.

Burness, et al., "The Effects of Nucleotides on Aspects of Neonatal Immunity," Nutrition, Sep. 1989, pp. 20–24.

Chandra, "Nutrients and Immune Function," Nutrition, Sep. 1989, pp. 25–31.

Carver, et al., "Dietary Nucleotides May Act as Growth Factors in Liver and Intestine," Fed. Soc. Exp. Biology, Abstract #3726, p. A643 (1993).

Carver, et al., "Dietary Nucleotide Effects Upon Immune Function in Infants," Pediatrics, 88(2):359 (1991).

Berlitz, et al., "Lehrbuch der Lebensmittelchemie," Springer–Verlag, p. 392 (1985).

Leach, et al., "Total Potentially Available Nucleosides of Human Milk by Stage of Lactation," Amer. J. Clin. Nutrition, V. 61; No. 6 (1995).

*Primary Examiner*—Helen Pratt
*Attorney, Agent, or Firm*—Donald O. Nickey; Thomas D. Brainard

[57] ABSTRACT

An improved enteral formula containing ribo-nucleotide equivalents (RNA, mono-, di- and triphosphate nucleotides, nucleosides and adducts such as activated sugars) at a level of at least 10 mg/100 Kcal (kilocalorie) of formula. More specifically, an infant formula containing at least 10 milligrams of nucleotide equivalents per 100 Kcal of formula where the nucleotide equivalents consist of RNA; mono-, di-, and triphosphate esters of adenosine, cytidine, guanosine, and uridine, and the d-ribose adducts thereof; and wherein the weight ratio of said cytidine nucleotide equivalents to said uridine nucleotide equivalents is 1.5:1 to 2.6:1; of said cytidine nucleotide equivalent to said adenosine nucleotide equivalents is 2:1 to 3.9:1; and of said cytidine nucleotide equivalents to said guanosine nucleotide equivalents is 1.75:1 to 2.8:1, is disclosed. The formula comprises carbohydrates, lipids, proteins, vitamins and minerals and four (4) ribo-nucleotide equivalents at specific levels and ratios. This invention also provides a dietary formula that enhances the immune system and alleviates diarrhea.

42 Claims, No Drawings

NUTRITIONAL FORMULA WITH RIBO-NUCLEOTIDES

This application is a continuation-in-part of U.S. patent application Ser. No. 08/178,687 filed Jan. 10, 1994 which is now U.S. Pat. No. 5,492,899.

FIELD OF THE INVENTION

The invention relates to an improved enteral nutritional formula and more particularly to infant formulas which contain ribo-nucleotide equivalents at a level of at least 10 mg/100 Kcal of formula and wherein the ribo-nucleotide components are at specific ratios.

BACKGROUND OF THE INVENTION

The composition of human milk serves as a valuable reference for improving infant formula. However, human milk contains living cells, hormones, active enzymes, immunoglobulins and components with unique molecular structures that cannot be replicated in infant formula. Unlike human milk, infant formula must remain stable on the shelf for up to thirty-six (36) months. These fundamental differences between human milk and infant formula often mandate differences in the composition to achieve similar clinical outcome.

Human milk has served as a valuable reference for improving infant formula. The investigation of human milk components has stimulated many investigations into what constituents may be added to infant formula. Greater knowledge of the composition of human milk affords the opportunity to design infant formulas that are closer to that of human milk. However, it becomes increasingly apparent that infant formula can never duplicate human milk. Many constituents in human milk are bioactive and because of synergies among these components there is little reason to believe that the same compound would have the same bioactivity in infant formula. The likelihood of this possibility is further diminished when the impact of heat treatment for sterilization and long-term storage of the formula is considered. The present invention is based, in part, on the concept of providing a formula which matches the performance of breast milk in most parameters without attempting to actually duplicate the delicate balance of human milk components.

The composition of human milk differs appreciably from that of other species and much attention has been paid to the various components. Several investigators have reported on the nucleotide content of milk from humans [Janas, L. M. et al: The Nucleotide Profile of Human Milk. Pediatr. Res. 16:659–662(1982) and Gil, A et al: Acid-soluble Nucleotides of Human Milk at Different Stages of Lactation. Journal of Dairy Research (1982). 49, 301–307.] The numerous publications cited in the Janas and Gil references also relate to the nucleotide composition of human milk and, in combination, leave one skilled in the art with a confused and conflicting understanding of the nucleotide composition of human milk. None of the prior art discloses the minimum level of nucleotide equivalents taught by the present invention nor the ratio of the four elements (adenosine, cytidine, guanosine and uridine) to each other. Most importantly the prior art does not suggest or disclose a formula that is superior to human milk in enhancing the immune response of a human.

Nucleosides are nucleotides minus the one to three phosphate groups. Nucleosides are a class of chemical compounds that are of importance in physiological and medical research. They may be obtained from the partial decomposition (hydrolysis) of nucleic acids. Nucleosides contain a purine or pyrimidine base linked to either d-ribose, forming ribosides, or d-deoxyribose, forming deoxyribosides. Representative of the nucleosides are adenosine, cytidine, guanosine, inosine and uridine.

Nucleotides (nucleosides plus at least one phosphate group) are the fundamental units of nucleic acids. The nucleotides found in nucleic acids are phosphate esters of the nucleosides. The term nucleotides is also sometimes applied to compounds not found in nucleic acids and which contain substances other than the usual purines and pyrimidines. The nucleotides inosine-5'-monophosphate and guanosine-5'-monophosphate are used as flavor potentiators.

Nucleotides are ubiquitous, low molecular weight compounds that participate in energy metabolism and modulation of enzymatic reactions. In addition, nucleotides are components of compounds that are crucial in the synthesis and catabolism of carbohydrates, lipids, protein, and nucleic acids. Clearly nucleotides and their metabolites are important determinants of numerous cellular processes.

Adequate cellular supplies of nucleotides in humans and animals are maintained by two pathways; the salvage pathway and de novo synthesis. The salvage pathway involves recovery of nucleotides and nucleosides liberated from metabolism (such as catabolized nucleic acids). De novo synthesis of nucleotides requires the precursors aspartic acid (aspartate), glutamine, glycine, and carbamoyl phosphate. The salvage pathway generally supplies sufficient quantities of nucleotides even in tissue with rapidly proliferating cells, including enterocytes, erythrocytes and immune cells. It is also known that addition of nucleotides to the diet inhibits the de novo pathway and activates the salvage pathway in the liver and extrahepatic tissue, especially in enterocytes.

Dietary sources rich in nucleotides include meats, fish, legumes, and dairy products. Nucleotides are primarily present in polymeric forms (DNA, RNA and nucleoproteins) in these foods and are degraded by ribonucleases, deoxyribonucleases and proteases, yielding nucleotides. Subsequent action of phosphatases yields nucleosides which appear to be the preferred form for absorption. Some additional digestion to free purine and pyrimidine bases may occur. Studies have been published that indicate that a specific transport system(s) exists for the absorption of nucleosides and bases.

Most dietary nucleotides are degraded, excreted, or utilized before reaching the systemic circulation. Although dietary nucleotides appear to have little access to the systemic circulation, they have been implicated as having numerous systemic effects. Reports indicate that dietary nucleotides influence the response to sepsis, alter blood lipid profiles, enhance brain function, and increase iron absorption, gut mucosal growth, and gut bifidobacteria populations.

U.S. Pat. No. 3,231,385 discloses and claims an active phosphatase free cow's milk which contains at least two of the respective disodium salts of (a) cytidine 5'-monophosphate in the amount of 10 to 20 mg/L of cow's milk, (b) guanosine 5'monophosphate in the amount of 0.2 to 0.4 mg/L of cow's milk, (c) uridine 5'-monophosphate in the amount of 1.2 to 1.4 mg/L of cow's milk, (d) guanosine 5'-diphosphate in the amount of 0.4 to 0.6 mg/L of cow's milk, (e) uridine 5'-diphosphate glucose in the amount of 0.5 to 1.0 mg/L of cow's milk, (f) uridine 5'-diphosphate galactose in the amount of 0.5 to 1.0 mg/L of cow's milk and (g) uridine 5'-diphosphate glucuronic acid in the amount of 1.0 to 3.0 mg/L of cow's milk.

U.S. Pat. No. 4,994,442 discloses and claims the addition of nucleosides and/or nucleotides to infant formula to provide a formula having enhanced physiological properties and methods of stimulation or repair of intestinal gut cells. This patent teaches and claims the use of at least one member selected from the group consisting of uridine, uridine phosphate, and mixtures thereof; guanosine, guanosine phosphate and mixtures thereof; adenosine, adenosine phosphate and mixtures thereof; cytidine, cytidine phosphate and mixtures thereof; and inosine, inosine phosphate and mixtures thereof. This patent also claims a method for enhancing the immune response of T-cells and for providing specific fatty acid phospholipid profiles in red blood cell membranes of infants. This patent fails to suggest the use of the four specific ribo-nucleotides disclosed in the present invention. This reference also fails to suggest the specific ratios and levels of ribo-nucleotides used in this invention and the surprising results relating to the immune system and diarrhea that are achieved through the present invention.

U.S. Pat. No. 5,066,500 discloses a non-milk based infant formula comprising carbohydrates, a source of amino acids, vegetable oils, minerals, vitamins, wherein the formula contains at least one of uridine, uridine phosphate or mixtures thereof; guanosine, guanosine phosphate or mixtures thereof; or adenosine, adenosine phosphate, or mixtures thereof; cytidine, cytidine phosphate, or mixtures thereof, or inosine, inosine phosphate, or mixtures thereof. This patent fails to disclose the four specific ribo-nucleotides utilized in the instant invention, the levels and ratios of those nucleotides in an enteral nutritional formula and the surprising results that can be obtained through the use of the instant invention.

U.S. Pat. No. 4,544,559 discloses and claims a nucleotide enriched humanized milk in powder form. The inventive aspect of this patent relates to the use of five (5) nucleotides in the precise ratios as follows: adenosine mono-phosphate (AMP) 1.32 mg/100 g, cytidine-monophosphate (CMP) 1.12 mg/100 g, guanosine-monophosphate (GMP) 1.49 mg/100 g, uridine-monophosphate (UMP) 3.42 mg/100 g and inosine-monophosphate (IMP) 0.45 mg/100 g of powdered formula. In contrast, the present invention only uses four (4) ribo-nucleotide equivalents, (as will be defined infra) those being represented by: cytidine 5'- monophosphate (CMP), uridine 5' monophosphate (UMP) guanosine 5' monophosphate (GMP) and adenosine 5' monophosphate (AMP). Also critical to the instant invention, is that these four ribo-nucleotides (or nucleotide equivalents) be present in the enteral formulation at a level of at least 10 milligrams of nucleotide equivalents per 100 Kcal of enteral formula. An even more specific aspect of the present invention, which sets it apart from the prior art is the requirement that the weight ratio of CMP to UMP be at least 1.5:1; that the ratio of CMP to AMP be at least 2:1; and the ratio of CMP to GMP be at least 1.75:1 (on a nucleotide equivalent basis). It should be understood that CMP, GMP, AMP and UMP refer to the various nucleotide equivalents of cytidine, guanosine, adenosine and uridine. Most preferably, the weight ratio of CMP:UMP is in the range of from about 1.5:1 to about 2.6:1; the weight ratio of CMP:AMP is in the range of from about 2:1 to about 3.9:1; and the weight ratio of CMP:GMP is in the range of from about 1.75:1 to about 2.8:1.

U.K. Patent 2,216,416 discloses a method of stimulating the immune function with the aid of a nucleobase source, the use of nucleobase sources for immuno stimulation and compositions comprising such nucleobase sources. Specifically, this patent relates to the administration of from 0.1 to 75 grams of RNA, DNA, nucleotides or nucleosides per day or an amount equivalent thereto in nucleobase form. This reference fails to suggest or disclose the specific benefits that can be realized through the use of four ribo-nucleotides at specific levels and ratios.

The enteral formula of the instant invention provides a positive advantage to the infant. The clinical studies which were conducted evidence the unexpected advantages of the instant invention. An additional aspect of the present invention is the overall balance of nutrient interactions and bio-availability, which provide an improved nutritional product. Another aspect of the present invention relates to an infant formula which meets the requirements of the Infant Formula Act and to methods for its production and analytical techniques for the determination of nucleotide equivalents.

Several investigators have reported that maternal milk contains factors that protect against diarrhea. These investigators have also reported that nucleotide-enriched formula have an effect on the incidence, duration and etiology of acute diarrhea. These investigators have failed to discover the specific nucleotides and ratios of the instant invention that are effacious in the treatment/prevention of diarrhea.

There has been much interest in this area of enteral nutritional formulations. The prior art is replete with various formulations using various ingredients. The general principle of adding RNA, DNA, nucleotides, nucleosides and/or nucleobases to food products is disclosed within the prior art. However, none of the prior art either taken individually or in any combination would suggest or predict, with any level of certainty, the discoveries the Applicants have made herein.

DISCLOSURE OF THE INVENTION

The term "nucleotide equivalents" as used herein means the total adenosine (A), cytidine (C), guanosine (G) and urigine (U) content present in any one or more of the following forms ribo-nucleosides, ribo-nucleotides, RNA, phosphate esters and d-ribose adducts of adenosine (A), cytidine (C), guanosine (G), and uridine (U). The various forms of A,C,G, and U are determined as the nucleoside and calculated and expressed as the monophosphate esters; adenosine monophosphate (AMP), cytidine monophosphate (CMP), guanosine monophosphate (GMP) and uridine monophosphate (UMP). These are the free acid forms of the monophosphate esters as opposed to the salt forms such as the mono or disodium salts. Some nucleotides are often sold as the sodium salts. For example, the sum inherent of adenosine plus adenosine from RNA, the mono-, di and triphosphate esters and the d-ribose adducts are stated as the nucleotide equivalent of the mono phosphate ester of adenosine. This invention relates only to the use of ribo-nucleotides and does not contemplate or claim the use of the deoxy form.

There is disclosed an enteral formula, said formula comprising: 1) protein, said protein being of a concentration of between 10 and 35 grams per liter of formula; (2) fat, said fat being of a concentration of between 20 and 45 grams per liter of formula: (3) carbohydrates, said carbohydrates being of a concentration of between 60 and 110 grams per liter of formula; and (4) at least 10 mg of nucleotide equivalents per 100 Kcal of formula, said nucleotide equivalents consisting of RNA; mono-, di-, and triphosphate esters of adenosine, cytidine, guanosine and uridine, and the d-ribose adjuncts thereof; and wherein the weight ratio of CMP:UMP is at least 1.5:1; of CMP:AMP is at least 2:1; and of CMP:GMP is at least 1.75:1. Most preferably, the weight ratio of CMP:UMP is in the range of from about 1.5:1 to about 2.6:1;

the weight ratio of CMP:AMP is in the range of from about 2:1 to about 3.9:1; and the weight ratio of CMP:GMP is in the range of from about 1.75:1 to about 2.8:1.

The minimum level of nucleotide equivalents in this invention is 10 mg per 100 Kcal of formula or 70 mg per liter of a formula having a caloric density of about 687 Kcal per liter. Levels of nucleotide equivalents at the claimed ratios above about 1.0 gms per liter of formula or about 100 mg/100 Kcal of formula is outside the scope of this invention. From this maximum level of about 100 mg/100 Kcal of formula or 1.0 g/liter of formula and the ratios set out above, the upper limits for each of the four-ribo-nucleotide components may be calculated.

There is also disclosed an enteral formula wherein the source of protein is selected from the group comprising condensed skim milk, non-fat milk, acid whey nucleotide equivalent reduced soy protein, milk protein concentrate and cheese whey. Milk protein concentrate is an ultra-filtered milk protein concentrate that has a reduced lactose content. In general, any appropriate source of protein can be used in this invention, including hydrolyzed proteins. There is further disclosed an enteral formula wherein the protein is 50–70% by weight condensed skim milk or non-fat milk and the fat is selected from the group consisting of soy oil, coconut oil, corn oil, high oleic safflower oil, fish oils, egg yolk oils, high oleic sunflower oils, microbial oils and fungal oils and mixtures thereof.

There is also disclosed an infant formula which comprises a nutritionally adequate source of amino nitrogen, carbohydrates, edible fats, minerals and vitamins; the improvement characterized in a composition comprising at least one member selected from each of the groups (a), (b), (c), and (d):

(a) uridine, uridine phosphates and mixtures thereof;

(b) guanosine, guanosine phosphates and mixtures thereof;

(c) adenosine, adenosine phosphates and mixtures thereof; and (d) cytidine, cytidine phosphates and mixtures thereof;

wherein the total amount of the composition is at least 10 mg per 100 Kcal of formula and wherein the weight ratio of CMP:UMP is at least 1.5:1 of CMP:AMP is at least 2:1; and of CMP:GMP is at least 1.75:1. Most preferably, the weight ratio of CMP:UMP is in the range of from about 1.5:1 to about 2.6:1; the weight ratio of CMP:AMP is in the range of from about 2:1 to about 3.9:1; and the weight ratio of CMP:GMP is in the range of from about 1.75:1 to about 2.8:1.

There is also disclosed an infant formula the improvement comprising adding from 29 to 39 mg of CMP per liter of formula; 15 to 20 mg of UMP per liter of formula; 10 to 15 mg of AMP per liter of formula and 14 to 20 mg of GMP per liter of formula. Preferably, the amounts of nucleotides are: CMP 30–33 mg; UMP 16–19 mg; AMP 11 mg and GMP 15–18 mg.

More specifically there is disclosed a formula wherein the protein is 50–70% condensed skim milk or non-fat milk and 30–50% cheese whey by weight and the fat has as its source soy, coconut and high oleic safflower oil.

The enteral formula according to the invention provides a source of carbohydrates selected from sucrose, corn syrup, glucose polymers and other carbohydrate sources. The formula may also contain dietary fiber. The teachings of U.S. Pat. No. 5,021,245 are incorporated herein by reference.

This invention also relates to a method of enhancing the immune system of a human, said method consists of feeding a human in need of treatment a formula, the improvement comprising a formula consisting essentially of: 1) protein, said protein being of a concentration of between 10 and 35 grams per liter of formula; 2) fat, said fat being of a concentration of between 20 and 45 grams per liter of formula; 3) carbohydrates, said carbohydrates being of a concentration of between 60 and 110 grams per liter of formula; and 4) at least 10 mg of nucleotide equivalents per 100 Kcal of formula and wherein the weight ratio of CMP:UMP is at least 1.5:1; of CMP:AMP is at least 2:1; and of CMP:GMP is at least 1.75:1. Most preferably, the weight ratio of CMP:UMP is in the range of from about 1.5:1 to about 2.6:1; the weight ratio of CMP:AMP is in the range of from about 2:1 to about 3.9:1; and the weight ratio of CMP:GMP is in the range of from about 1.75:1 to about 2.8:1. There is also disclosed a novel method of producing an enteral formula containing nucleotides and its use to treat or prevent diarrheal disease and to novel analytical techniques.

There is also disclosed a method for manufacturing infant formula, said method comprising the steps of: 1) dispersing an appropriate quantity of protein in water or oil sufficient to solubilize or suspend the protein, thereby forming a protein solution; 2) dissolving carbohydrates in water, thereby forming a carbohydrate solution; 3) mixing minerals in water or the carbohydrate solution, thereby forming a mineral solution or a mineral/carbohydrate solution; 4) combining appropriate quantities of said protein solution, said carbohydrate solution, said mineral solution, and a solution of oils containing oil soluble vitamins, 5) heat processing and homogenizing the combined solution; 6) adding water soluble vitamins, iron, choline and other nutrients to the combined solution; 7) adding water to dilute the combined solution to the desired caloric density, approximately 400–725 kcal per liter of formula and 8) adding from 29 to 39 mg of CMP per liter of formula; 15 to 21 mg of UMP per liter of formula; 10 to 16 mg of AMP per liter of formula and 14 to 20 mg of GMP per liter of formula directly to the batch or in the form of an aqueous solution.

As used herein, the terms CMP, UMP, GMP and AMP mean not only the monophosphates of adenosine, cytidine, guanosine and uridine butal so their nucleotide equivalents which include polymeric RNA, ribo-nucleosides, ribo-nucleoside-containing adducts and di- and triphosphate ribo-nucleotides.

There is also disclosed a novel analytical technique that can quantify the various forms of the four nucleotides in complex food matrices. The analytical process comprises: 1) the enzymatic digestion of polymeric RNA to nucleotide 2) the enzymatic co-digestion of nucleoside containing adducts to nucleosides and the nucleotides to nucleosides 3) the covalent attachment of the enzymatically released nucleosides plus the inherent nucleosides to boronic acid that has been immobilized on a polyacrylamide gel 4) the release of the nucleosides from the boronate derivatized polyacrylamide gel via a pH shift 5) the separation of the nucleosides via low pH reverse phase/ion pairing HPLC using octane sulfonate as the ion-pairing agent and 6) quantitation of the nucleoside via U.V. absorbance using external standards or other means known in the art of analytical chemistry.

There is also disclosed a novel anti oxidant system that is used in the enteral formulas according to this invention. The antioxidant system consists of β-carotene, R,R,R, α-tocopherol and selenium. The level of R,R,R, α-tocopherol can range from 10 to 30 IU per liter of formula. The level of β-carotene can range from 375 to 575 µg per liter of formula and the level of selenium can range from 14 to 32 mcg per liter of formula. The selenium used in this aspect of the invention may be delivered in the form of selenate. The teachings of U.S. Pat. No. 5,221,545 are herein incorporated by reference.

In actual use, the formula of this invention may be consumed by any infant and should be in compliance with accepted levels of vitamins, minerals, micro-components and the like. The amount consumed does not differ from that associated with the normal consumption of commercially available infant formula.

A representative formula for the enteral nutritional product of the invention is set forth in Table I.

TABLE I

FORMULA ACCORDING TO THE INVENTION

| Nutrient | Concentration per liter of formula |
| --- | --- |
| Protein | 13.0–20 g |
| Protein Source | |
| CSM[1] | 55–75% |
| | 7.15–15 g |
| WPC[2] | 25–45% |
| | 3.25–9.0 g |
| Lipid | 13–21 g |
| H.O. Safflower Oil | 35–55% |
| Soy Oil | 20–40% |
| Coconut Oil | 20–45% |
| Carbohydrate lactose | 70–110 mg |
| Nucleotides | 70–100 mg |
| CMP | 29–39 mg |
| UMP | 15–21 mg |
| AMP | 10–16 mg |
| CMP | 14–20 mg |
| Iron | 8–16 mg |
| R,R,R,α tocopherol | 10–30 IU |
| βCarotene | 375–575 µg |
| Selenium | 14–32 mcg |
| Calcium | 475–850 mg |
| Phosphorus | 240–700 mg |
| Ca:P Ratio | 1.4 to 2.4 |

[1]CSM is Condensed Skim Milk
[2]WPC is Whey Protein Concentrate

The pediatric nutritional formula of this invention is generally prepared using the following method. An appropriate quantity of protein is dispersed in sufficient water or oil to solubilize or suspend it, thereby forming a protein solution/suspension. Typically this protein source would be intact milk proteins and/or hydrolyzed milk proteins. Vegetable proteins, such as soy protein, can also be used provided the high inherent levels of nucleotide equivalents have been removed. A carbohydrate source such as one or more of corn syrup solids, lactose maltodextrins and sucrose is dissolved in water, thereby forming a carbohydrate solution. A source of dietary fiber, such as soy polysaccharide, may also be added. Appropriate minerals are dissolved in water, the carbohydrate solution or oil, so as to form a mineral solution.

Once formed, the three solutions (protein, carbohydrate, and mineral) are combined in appropriate quantities with oils and oil soluble vitamins. This resulting solution is then heat processed and homogenized. Following processing, water soluble vitamins, iron, choline and other nutrients are added and then the nucleotides are added. The solution is then diluted with water to the appropriate caloric density, approximately 400–725 kcal per liter of formula. The formula is then dispensed into containers and retorted to obtain commercial sterility or packaged aseptically using commercially available techniques and equipment. As prepared, the formula contains appropriate nutrients in compliance with the Infant Formula Act as of the date of this application. It should also be recognized that the unique formula of this invention could be prepared for use in powdered form or as a concentrated liquid.

The invention will be better understood in view of the following examples, which are illustrative only and should not be construed as limiting the invention.

DETAILED DESCRIPTION OF THE INVENTION

Analytical Techniques

One feature of the instant invention resides in the novel analytical technique used to identify and quantify the nucleotide equivalents useful in this invention. Analysis of certain starting materials, especially the protein, will determine the actual amount of nucleotides to be added. This analysis of the raw materials of the formula is critical to determine what nucleotides, if any, are contained in the starting materials. The analytical method is also critical to determine the proper ratios of the nucleotides to each other. The analytical method according to this invention will determine nucleotide equivalent levels in complex food matrices. The method in general exploits the enzymatic digestion of various forms of ribonucleic acids to the simple monomeric ribonucleosides and the ability of the cis-diol groups of ribonucleosides to form a pH dependent covalent complex with boronic acid. Boronate derivatized polyacrylamide gel is used to very selectively prefractionate ribonucleoside directly from complex matrices. The isolated ribonucleosides are subsequently separated via low pH reverse phase/ion-pairing HPLC using octanesulfonate as the ion-pairing agent. Ribonucleosides are detected via UV absorbance, and the corresponding levels are determined by comparison to external standards. The method can be used to quantitate inherent levels of ribonucleoside in foods. Because of the selective prefractionation, the method is essentially matrix independent. It should be understood that the novel analytical technique of this invention will not detect nucleosides from DNA or any form of nucleic acid that does not contain the cis-diol groups of ribose. It has been used to determine ribonucleic acid types and levels in infant and medical nutritional products, human milk, protein commodities, and clinical and commercial animal chows.

The following is an example of the analytical technique of this invention that can be used to determine the presence and ratios of the nucleotide equivalents.

EXAMPLE I

Analysis of Similac® with Iron

To a 10 ml Reacti-Therm vial with stir bar was placed 2.0 ml of Similac® with Iron (a non-fat milk protein infant formula produced by the Ross Products Division of Abbott Laboratories, ready to feed form, 676 Kcal per liter) 3.0 ml of 50 mM sodium acetate at pH 5.1, 50 µl of 10 mM zinc sulfate and 50 µl of the enzyme preparation nuclease P1 (Sigma Chemical). The enzyme preparation was 5 mg of dry enzyme powder, as received from Sigma, and 4 ml of 50 µM sodium acetate at pH 5.1. The mixture was heated to 37° C. and stirred for 16 hours. This reaction converted the polymeric RNA to monomeric 5' mono-nucleotides.

To the same reaction vial was added 50 µl of 30% ammonium hydroxide, 1 ml of 0.5M ammonium acetate (pH 8.75), 50 µl of 1.0M magnesium chloride, 50 µl of bacterial alkaline phosphatase (BAP) (Sigma Chemical as a suspension) and 50 µl of a nucleotide pyrophosphatase enzyme preparation (Sigma Chemical). The pyrophosphatase enzyme preparation was 5 mg of dry powder in 4 ml of 0.5M ammonium acetate buffer. The mixture was incubated at 37° C. for three hours. This reaction converted the nucleoside containing adducts and the nucleotides to the ribonucleosides.

The reaction mixture was transferred to a 50 ml volumetric flask using 25 ml of 0.5M sodium phosphate, pH 10.5. Water was added to a final volume of 50 ml. The sample mixture was shaken and may be filtered to remove insoluble protein.

5 grams of dried Affi-Gel-601, boronate derivatized (from Bio-Rad) was hydrated in 50 ml of 100 mM phosphate buffer at pH 6.5. To a 10 ml open column was added the hydrated Affi-Gel-601 to obtain a packed volume of about 1 ml. The gel was converted to the basic form by washing with 5 ml aliquots of 0.25M sodium phosphate buffer, pH 10.5, until the gel no longer swelled. The gel was now about 2 ml in volume. The gel was resuspended in the buffer to maintain adequate flow.

To the prepared gel was added 10 ml of the sample that was previously treated with the enzymes and the eluant was discarded. At this point, the nucleosides are covalently attached, through the cis-diol groups, to the boronic acid gel. The gel was washed with 20 ml of 0.25M sodium phosphate, pH 10.5 and the eluant was discarded. The nucleosides were eluted and collected in a 10 ml volumetric flask by adding 2 ml of 1.0M phosphoric acid to the column followed by 5 ml of 0.1M phosphoric acid. At this point the nucleosides have been isolated from the sample and are now ready to be characterized.

The volumetric flask was brought to a final volume of 10 ml with water. The sample was then placed on a HPLC for separation and quantification of nucleosides using external standards. The nucleosides were separated via low pH, reverse phase, ion pairing chromatography using an acetonitrile gradient. The nucleosides were detected by U.V. absorbance at 260 nm and 280 nm. Nucleosides were quantified by reference to external standards and the results were converted to the corresponding monophosphate nucleotide value by multiplying the nucleoside value by the molecular weight ratio of the monophosphate nucleotide over the nucleoside. The results were expressed as mg/L, of mononucleotide.

| NUCLEOTIDES IN SIMILAC ® WITH IRON | | |
| --- | --- | --- |
| uridine - 3–5 | guanosine - trace | adenosine - trace |
| inosine - trace | cytidine - 1–3 | |

It should be noted that some samples have been found to be active with respect to nucleic acid degradation. Of particular concern is the enzymatic conversion of AMP to IMP. Heat inactivation has proven to be effective in rendering the sample inactive. The procedure for heat inactivation is to heat the sample to over 100° C. for at least 15 minutes. After the sample has cooled, buffer, enzyme, and zinc are added and the first hydrolysis is carried out.

This analytical technique was used on raw materials to determine base line nucleotide content and on final clinical product to confirm the presence and concentration of the four nucleotides used in the invention.

EXAMPLE II

Preparation of Enteral Formula

On a commercial scale, a control and an experimental formula according to the invention were prepared having the compositions set forth in Table II. The two formula are as close as possible to being identical except for the nucleotide components.

TABLE II

| COMPOSITION OF STUDY FEEDINGS | | |
| --- | --- | --- |
| Nutrient | CON (Control) | NUC (Formula of the Invention) per liter |
| Protein, g | 14.0 | 14.4 |
| Fat, g | 36.5 | 38.3 |
| Carbohydrate, g | 77.1 | 75.5 |
| Calcium, mg | 544.4 | 532.5 |
| Phosphorus, mg | 295.0 | 316.2 |
| Magnesium, mg | 73.5 | 77.7 |
| Sodium, mg | 170.1 | 179.2 |
| Potassium, mg | 931 | 948.6 |
| Chloride, mg | 487.7 | 493.2 |
| Iron, mg | 14.0 | 14.0 |
| Zinc, mg | 5.1 | 5.1 |
| Copper, mcg | 608 | 608 |
| Iodine, mcg | 61 | 61 |
| Manganese, mcg | 34 | 34 |
| Vitamin A, IU | 2930 | 2970 |
| Vitamin D, IU | 405 | 405 |
| Vitamin E, IU | 24.6 | 24.8 |
| Vitamin K, mcg | 54 | 54 |
| Vitamin C, mg | 170 | 172 |
| β-Carotene, mcg | 450 | 450 |
| Selenium, mcg | 23 | 23 |
| Thiamin, mcg | 1350 | 1360 |
| Riboflavin, mcg | 1014 | 1014 |
| Pyridoxine, mcg | 480 | 480 |
| Vitamin $B_{12}$, mcg | 1.7 | 1.7 |
| Niacin, mcg | 7095 | 7095 |
| Folic acid, mcg | 101 | 101 |
| Pantothenic acid, mcg | 3041 | 3041 |
| Biotin, mcg | 30 | 30 |
| Taurine, mg | 45 | 45 |
| Choline, mg | 108 | 108 |
| Inositol, mg | 32 | 32 |
| Energy, Kcal | 676 | 676 |
| CMP, mg | 2.72* | 31.2 |
| UMP, mg | 4.19* | 17.7 |
| AMP, mg | 0.57* | 9.8 |
| GMP, mg | 0.45* | 14.4 |

*-inherent levels from raw materials

In this example, a 7711 Kg batch of the formula according to the invention was prepared (NUC). The control formula (CON) was prepared in a similar fashion except the addition of the nucleotides was omitted. The list of ingredients and amounts are found in Table III.

TABLE III

| Ingredients and Amounts for NUC Formula | |
| --- | --- |
| Ingredient | Amount |
| High Oleic Safflower Oil | 120.2 Kg |
| Coconut Oil | 85.7 Kg |
| Soy Oil | 80.3 Kg |
| Lecithin | 2.92 Kg |
| Mono- and diglyceride | 2.92 Kg |
| Oil Soluble Vit. Premix | 0.365 Kg |
| βCarotene | 0.0137 Kg |
| Carrageenan | 1.43 Kg |
| Whey Protein Concentrate | 61.2 Kg |
| Lactose | 476.3 Kg |
| Potassium Citrate | 4.6 Kg |
| Magnesium Chloride | 0.735 Kg |
| Low Heat Condensed Skim Milk | 821 Kg |
| Calcium Carbonate | 3.36 Kg |

TABLE III-continued

Ingredients and Amounts for NUC Formula

| Ingredient | Amount |
| --- | --- |
| Ferrous sulfate | 0.450 Kg |
| Water Soluble Vitamin Premix Trace Minerals/ Taurine | 1.11 Kg |
| Choline Chloride | 0.600 Kg |
| Adenosine 5'monophosphate | 0.113 Kg |
| Guanosine 5'monophosphate-Na2 | 0.197 Kg |
| Cytidine 5' monophosphate | 0.259 Kg |
| Uridine 5'monophosphate-Na2 | 0.216 Kg |
| Ascorbic Acid | 1.78 Kg |
| 45% KOH | 2.36 Kg |

Total Yield 7711 Kg

The first step is the preparation of the oil blend. To an appropriately sized blend tank with agitation and heating soy oil, coconut oil and high oleic safflower oil were added. The mixture was heated to 73.8°–79.4° C. The lecithin and mono- and diglycerides (Myverol 18-06) were added to the blend tank with agitation. The oil soluble vitamin premix was added with agitation. The premix container was rinsed with the oil blend and transferred back to the blend tank to ensure complete delivery of the vitamin premix. The beta-carotene was added to the oil blend and the mixture agitated until the components were well dispersed. The beta-carotene container was rinsed with the oil blend and the contents returned to the blend tank to ensure complete delivery of the beta-carotene solution. Lastly, the carrageenan was added to the oil blend and the mixture was agitated and held at 54.4°–60° C. until used.

The carbohydrate, mineral and CSM (condensed skim milk) protein slurry was prepared next. To water heated to 68.3°–73.8° C. the lactose was added and the mixture agitated until the lactose was well dissolved. Potassium citrate was then added followed by potassium chloride, sodium chloride and magnesium chloride. The condensed skim milk (CSM) was then added. Tri-calcium phosphate was added, the mixture agitated and held at 54.5°–60° C. until used.

The protein-in-water (PIW) slurry was then prepared. The whey protein concentrate was added to water at 54.5°–60° C. under mild agitation. The PIW slurry was held under mild agitation until needed. Also contemplated in this invention is the use of protein-in-fat (PIF) slurries, wherein an appropriate amount of protein is admixed with all or a portion of the oil component.

The PIW slurry was then added to the prepared oil blend. The required amount of the carbohydrate, mineral and CSM slurry was then added to the oil blend. The pH of the mixture was then determined and if below specification it was adjusted using KOH to a pH of 6.75 to 6.85. The mixture was then held at 54.4°–60° C. under agitation for at least 15 minutes.

The mixture was then heated to 68.3°–73.8° C. and deaerated under vacuum. The mixture was then emulsified through a single stage homogenizer at 6.21 to 7.58 MPa.

After emulsification, the mixture was heated to 120°–122° C. for 10 seconds and then 149°–150° C. for 5 seconds. The mixture was then passed through a flash cooler to reduce the temperature to 120°–122° C. and then through a plate cooler to reduce the temperature to 71.1°–79.4° C. The mixture was then passed through a two stage homogenizer at 26.89 to 28.27 MPa and 2.76 to 4.14 MPa. The mixture was held at 73.9° to 83.2° C. for 16 seconds and then cooled to 1.1° to 6.7° C. At this point, samples are taken for microbiological and analytical testing. The mixture was held under agitation.

A calcium carbonate solution may be prepared for use in adjusting the calcium level of the mixture if outside of specification.

A vitamin stock solution was prepared. To water heated to 37.8° to 65.6° C. was added potassium citrate and ferrous sulfate. The vitamin premix was then added and the mixture agitated. The choline chloride was added and then the required amount of this vitamin mixture was added to the batch.

The nucleotide solution was then prepared. The following nucleotides were added to water with mild agitation in the following order: AMP, GMP, CMP, UMP. Agitation was continued for about 10 minutes to dissolve the nucleotides. The nucleotide solution was then added to the batch. This is one critical aspect of the invention. It is extremely important that the nucleotides be added after the homogenizations and heat treatments. Numerous experiments have been conducted that have shown the addition of the nucleotides at any other point will result in degradation of the nucleotides and thereby change the specific levels and ratios as claimed. It is believed that AMP is converted to IMP through the presence of adenosine deaminase in the raw materials, especially the protein components.

Lastly, an ascorbic acid solution was prepared and added slowly to the batch with agitation for at least 10 minutes. Final dilution with water to meet specified levels of solids and caloric density was completed. The batch was then packaged in 32 ounce metal cans and sterilized using conventional technology.

EXAMPLE III

Clinical Study of Enteral Formula

The purpose of the clinical investigation was to determine the effect of a nucleotide-fortified formula according to the present invention on the development of the neonatal immune system in infants as measured by the antibody response to childhood vaccines.

This was a 12-month, randomized, controlled, blinded, multi-site trial of term infants. Infants enrolled into the study received human milk (HM) or one of two clinically labelled formulas: 1) control formula (CON) or 2) CON formula supplemented with nucleotides (NUC). The analyzed composition of each formula is set forth in Table II. A total of 311 infants completed the study (107 CON, 101 NUC, 103 HM). Infants followed the immunization schedule recommended by the American Academy of Pediatrics with single lots of Hib TITER® Hemophilus influenzae type b conjugate vaccine (Diphtheria CRM 197 and tetanus protein conjugate sold by Lederle, Inc.) and Diphtheria and Tetanus Toxoids and Pertussis Vaccine Adsorbed, sold by Lederle, Inc. Infants were full-term with a gestational age of 38–42 weeks, at or above the 5th percentile for weight, length, and head circumference and were enrolled between 2 and 10 days of age. All subjects were healthy with no indication of systemic disease and did not receive any medications, mineral, or vitamin supplements.

The primary outcome variable investigated was vaccine response at 6, 7, and 12 months of age. Also investigated were differential white blood cell count, lymphocyte subset analysis, NK activity, and lymphoblast transformation in response to specific and non-specific stimuli at 2, 6, 7, and 12 months of age. Secondary outcome variables included intake, anthropometry, and indices of tolerance (stool characteristics and incidence of spit-up).

Also investigated was the antioxidant status of infants fed the formula according to the present invention which contained the novel antioxidant system of: 10–30 IU of R, R, R, α-tocopherol per liter of formula, 375–575 µg of β-carotene per liter of formula and 14–32 mcg of selenium per liter of formula.

During infancy, as in adulthood, the body has a number of antioxidant systems to protect against injury from free radicals, the products of oxidation. The antioxidant system of this invention was clinically proven to promote the anti oxidant status of the infant greater than currently available infant formula. This improved antioxidant status was demonstrated as a function of increased levels of plasma Vitamin E, reduced levels of plasma lipid peroxides, and increased free radical trapping capacity.

Experimental Design

At 2, 4, and 6 months of age DPT and Hib vaccines were administered. Blood samples were obtained by venipuncture at 2, 6, 7, and 12 months of age. When vaccines were administered the blood sample was obtained before the inoculation. Parents of the infants agreed to feed the infant only study formula until 4 to 6 months of age when table foods were added to supplement the study formula. The HM fed group were exclusively breast fed up to 2 months of age and a mixture of HM and Similac® with Iron (Ross Products Division of Abbott Laboratories) after 2 months, if necessary.

Weight, length and head circumference were measured at 21 days of age and at 2, 4, 6, 7, and 12 months of age. Three-day records of formula intake, frequency of spit-up and vomiting and the frequency, color and consistency of stools were used to assess tolerance. Blood samples (2 mL) were drawn at 2 months of age and transferred directly into a heparin-containing tube, and gently inverted. At 4, 6, 7, and 12 months of age 5 mL of blood was collected. Two and a half mL were transferred to heparinized tubes and 2.5 mL to a plain tube without an anti-coagulant. Tubes of blood were carefully packed in thermally insulated containers and shipped to the laboratory for analysis.

Radial immunodiffusion assays were performed using standard kits purchased from The Binding Site, Inc (5889 Oberlin Drive, Suite 101, San Diego, Calif. 92121) for the measurement of serum or plasma IgG and IgA.

The detection of tetanus and diphtheria IgG was accomplished as follows. Tetanus toxoid antigen (Connaught) was diluted in 0.05M carbonate buffer (pH 9.6) to 2 µg/mL, added to the wells of microtiter plates at 200 µL per well, and incubated at room temperature for 1 hour. Diphtheria toxoid antigen (Connaught) was diluted in the same manner to 15 µg/mL. The coated plates were washed three times in PBS containing 0.05% chicken egg albumin and 0.1% Tween 20. Samples and positive control tetanus and diphtheria toxoid immune globulin, were diluted in PBS/albumin/Tween, added to triplicate wells at 200 µL/well, and incubated at room temperature for 1 hour. PBS alone was also added to triplicate wells to provide a blank. Plates were again washed three times in PBS/albumin/Tween. Affinity purified horseradish peroxidase-conjugated goat anti-human IgG (The Binding Site, Inc) was diluted in PBS/albumin/Tween, added to the microtiter plates, and again incubated at room temperature for 1 hour. Tetramethylbenzidine (TMB) substrate (Kirkegaard and Perry Laboratories) was added to all wells at 100 µL/well, and incubated at room temperature for 10 minutes. The substrate reaction was stopped by adding 100 µL of 1M phosphoric acid per well. Optical density of each well was measured using a wavelength of 450 nm. Sample units were calculated based on the tetanus and diphtheria toxoid immune globulin standards. See Sedgurch and Bolton; *J Clin Microbiol.* 1983;18:104–109.

Serum IgG directed against Haemophilus influenzae type b capsular polysaccharide (Hib) antigen was detected using a modified version of the procedure described by Anthony et al; *J Clin Microbiol* 1982;16:350–354. The modifications are described in Granoff, et al; *J Infect Dis* 1986;154:257–264.

Concentrations of total serum antibody to the Hib antigen were measured by a radioactive antigen-binding assay (Hib Farr) using the procedure described by Granoff et al; *J Infect Dis* 1986;154:257–264. The Hib antigen was purified and labeled with iodine. A reference serum pool from the US Bureau of Biologics (Rockville, Md.) was used to standardize the assay. The smallest amount of immunoglobulin detectable was 0.025 µg/mL serum, as determined with this reference pool.

Natural killer cell (NK cell) activity was measured using Histopaque-purified peripheral blood lymphocytes. The cytotoxicity of the NK cells was measured using procedure described by Wierda et al., *J Immunol. Methods* 1989; 122:15–24.

Statistical Methods

The immunological variables were analyzed in two different ways. For the variables relating directly to vaccine response (Hib Farr, Hib IgG, tetanus, diphtheria, total IgG and IgA) the variables were transformed by taking logarithm base 10 and doing Analysis of Variences (ANOVAs). The procedure is commonly used in the vaccine literature.

Anthropometric data were analyzed for each gender separately. Analysis of Varience (ANOVA) was done at birth, initial visit, 2, 4, 6, 7, and 12 months of age for weight, length and head circumference. Weight gain, length gain and head circumference gain were also analyzed by ANOVAs. Intake data were ranked and analyzed by ANOVAs (number of feedings, volume intake, percent of feedings with spit-up, vomits or both). Stool variables were ranked and analyzed with ANOVAs (number of stools, mean rank consistency and percent of stools with gas or unusual odor).

RESULTS

Substantial amounts of data were collected on each of the 311 infants enrolled in this clinical investigation. Disclosure of all this information is outside the scope of this document, however, the following is a summary of the information that supports the novel and unobvious features of the instant invention.

Vaccine antibody response data was statistically analyzed by two methods. Table IV shows the medians of the variables in the original units. The ANOVA was performed on medians of ranked data. Table V shows geometric means. For this analysis, the variables were transformed by taking logarithm base 10, and the ANOVA compared the mean of the logs. The mean of the logs converted back to the original units is the geometric mean. Use of geometric means is commonly used in the vaccine literature. At 7 months of age, infants in the NUC group had a higher antibody ($P<0.05$) response than the CON or HM group to Hib vaccine (geometric mean of 7.24 vs 4.05 or 4.2 µG Ig/mL, respectively by the Hib Farr assay). The NUC group had a higher response than the HM group to diphtheria toxoid vaccine (geometric means of 1.77 vs 1.29 U diphtheria toxoid specific IgG/mL, respectively). The enhanced antibody response to Hib vaccine persisted through 12 months of age as seen in Table V.

There were no differences in NK activity at any time, and the differential white count, lymphocyte subsets, and lymphoblast transformation was very similar among all groups. The primary differences were at 12 months of age, when infants fed HM had more white blood cells, monocytes, lymphocytes, CD3, and CD19 cells than CON (P<0.05). The NUC group was intermediate and not statistically different. Infants fed HM had greater numbers of NK cells (CD3−, CD16+, CD56+) than formula-fed (CON or NUC) infants (P<0.05). The NUC group had a higher percent CD4 cells than HM-fed infants (P<0.05) throughout the study.

Growth of infants was similar in all three groups. Tolerance and intake was similar for the two formula groups.

The similarity in growth and tolerance among all infants demonstrated that both formulas are acceptable. Likewise, the similarity in measures of immune system components among infants fed formulas or HM demonstrates that all feedings promote development of the immune system within normal ranges, however, for the first time an immune enhancement as measured by vaccine response to H. influenzae b and diphtheria toxoid is reported for infants consuming infant formula (NUC).

The consistently enhanced vaccine response of infants fed NUC vs CON suggests that nucleotides play an important function in immunological development of the infant.

DETAILED DISCUSSION OF RESULTS

Immunological Parameters

Vaccine response data are provided in Table IV as reported from the assays and Table V as geometric means. The antibody response to the Hib vaccine was measured as Hib Farr (μg Ig/mL). NUC-fed infants had significantly higher levels of Hib Farr antibody than infants fed HM at 6 months (0.43 vs 0.30, P<0.05) higher than infants fed CON or HM at 7 months (7.7 vs 3.62 and 5.40, respectively, P<0.05) and at 12 months (1.35 vs 0.68 and 0.82, respectively, P<0.05). Hib response was also measured as Hib specific IgG, and the results paralleled the Hib Farr values at 6 and 7 months. This parameter was not measured at 12 months.

Response to the diphtheria vaccine was measured as diphtheria toxoid specific IgG. There were no differences between groups at 6 or 12 months, but at 7 months infants fed NUC had a significantly (P<0.05) higher response (1.77 U/mL) than infants fed HM (1.29 U/mL). See Table V. There were no differences at any time point for tetanus specific IgG.

TABLE IV

| | VACCINE RESPONSE Median (n) | | |
|---|---|---|---|
| | NUC | CON | HM |
| | 6 months | | |
| Hib Farr (μg Ig/mL)[1] | 0.43 (93)[a] | 0.36 (96)[a, b] | 0.30 (97)[b] |
| Hib IgG (mg/mL) | 0.06 (94)[a] | 0.06 (101)[a, b] | 0.03 (99)[b] |
| Diphtheria IgG (U/mL) | 0.47 (78) | 0.32 (85) | 0.36 (80) |
| Tetanus (IgG (U/mL) | 0.71 (80) | 0.72 (82) | 0.53 (80) |

TABLE IV-continued

| | VACCINE RESPONSE Median (n) | | |
|---|---|---|---|
| | NUC | CON | HM |
| | 7 months | | |
| Hib Farr (μg Ig/mL) | 7.70 (94)[a] | 3.62 (101)[b] | 5.40 (99)[b] |
| Hib IgG (mg/mL) | 1.25 (93) | 0.63 (101) | 0.60 (97) |
| Diphtheria IgG (U/mL) | 1.70 (85)[a] | 1.53 (89)[a, b] | 1.42 (90)[b] |
| Tetanus IgG (U/mL) | 5.01 (86) | 4.47 (90) | 4.75 (91) |
| | 12 months | | |
| Hib Farr (μg Ig/mL) | 1.35 (89)[a] | 0.68 (94)[b] | 0.82 (95)[b] |
| Hib IgG (mg/mL) | ND[3] | ND | ND |
| Diphtheria IgG (U/mL) | 0.30 (82) | 0.24 (87) | 0.30 (84) |
| Tetanus IgG (U/mL) | 0.92 (83) | 0.84 (87) | 0.90 (85) |

[1]Values in the same horizontal row with different superscripts (a or b) are significantly different, P < 0.05.
[2]p < 0.05, no pairwise differences
[3]ND = not determined

TABLE V

| | VACCINE RESPONSE Geometric Mean (n)[1] | | |
|---|---|---|---|
| | NUC | CON | HM |
| | 6 months | | |
| Hib Farr (μg Ig/mL) | 1.30 (93)[a] | 1.24 (96)[a, b] | 1.23 (97)[b] |
| Diphtheria IgG (U/mL) | 0.36 (78) | 0.28 (85) | 0.33 (80) |
| | 7 months | | |
| Hib Farr (μg Ig/mL) | 7.24 (94)[a] | 4.05 (101)[b] | 4.21 (99)[b] |
| Diphtheria IgG (U/mL) | 1.77 (85)[a] | 1.38 (89)[a, b] | 1.29 (90)[b] |
| | 12 months | | |
| Hib Farr (μg Ig/mL) | 1.41 (89)[a] | 0.76 (94)[b] | 0.85 (95)[b] |
| Diptheria IgG (U/mL) | 0.33 0.25 (82)(87) | 0.27 (84) | |

[1]Values in the same horizontal row with different superscripts (a or b) are significantly different; p < 0.05.
[2]p < 0.05, no pairwise differences It is generally accepted that a Hib FARR level of antibody greater than 1 μg of Ig/mL one month after immunization imparts protection to the infant. The percent of infants who had this level of protection was determined from the data set and is set forth in Table VI. The infants fed the NUC formula consistently had a 10% greater protection rate than infants in the other two groups.

TABLE VI

| HIB PROTECTION RATE (% of subjects with > 1 μg anti-Hib Ig (mL) | | | |
|---|---|---|---|
| | NUC | CON | HM |
| 6 months | 28% | 18% | 16% |
| 7 months | 90% | 80% | 80% |
| 12 months | 55% | 44% | 45% |

Natural killer (NK) cell activity was similar in all three groups. HM group had significantly higher numbers of NK cells (P<0.05) than NUC at 2, 6, and 12 months and CON at 2, 7, and 12 months. Formula-fed infants had a higher percent CD4 cells at 2 months (NUC, CON>HM; P<0.005), 7 months (CON, NUC>HM; P<0.01), and 12 months (NUC>HM; P<0.05). The NK activity data are presented in Table VII.

TABLE VII

| | NK ACTIVITY[1] | | |
|---|---|---|---|
| | NUC | CON | HM |
| 2 months | 11.2 | 8.0 | 9.0 |
| 6 months | 9.0 | 12.6 | 9.0 |
| 7 months | 13.9 | 14.3 | 13.0 |
| 12 months | 19.4 | 21.3 | 21.4 |

[1]Values are % target cells killed at effector:target ratio of 50:1.

Part of the impetus for this study and evidence that different ratios and levels of nucleotides impact on different physiological parameters was the report by Carver et al. (*Pediatrics* 1991;88:359) that infants fed nucleotide-fortified SMA® (infant nutritional sold by Wyeth, Inc. believed to contain 21 mg CMP; 6.0 mg AMP; 6.0 mg UMP; 6.0 mg AMP and 3.0 mg IMP per liter of formula) had significantly higher NK activity than those fed unfortified SMA. The present study, using the formula according to the instant invention, shows no effect of nucleotides on NK activity at 2 months and in fact no difference, among any of the groups at any time. Given the small number of infants in the Carver study (42 degrees of freedom at 2 months) compared to this study (255 degrees of freedom at 2 months), it would seem likely the Carver data are an aberration due to small sample size or, the addition of nucleotides does not increase number of NK cells or, the types and levels of nucleotides used by Carver produced only a cellular response as opposed to the humoral response seen in this invention.

The anthropometric measurements indicate that growth was comparable among all infants in the study. The fact that even before controlling for birth values there were no differences among males for weight, length, or head circumference gives assurance that growth was acceptable among all groups.

The higher stool frequency and number of feedings per day of HM-fed infants compared to formula-fed infants during the first 2 months is well established. Softer stools of HM-fed infants are also common, although only the NUC group was different at 2 months and by a small amount. Overall, the measures of tolerance among all groups were very similar through 4 months when half the infants were still being exclusively breast-fed. These data demonstrate both formulas were extremely well tolerated and are set forth in Table IX.

TABLE IX

| INTAKE SAND TOLERANCE Mean (SEM)[1] | | | |
|---|---|---|---|
| | NUC | CON | HM |
| *2 months* | | | |
| | 100 | 107 | 103 |
| Feedings (#/day) | 6.1 (0.1) | 6.4 (0.1) | 7.7 (0.2) |
| Intake (mL/day) | 831 (19) | 823 (18) | ND |
| Spit-up (% of feedings) | 8 (2) | 18 (2) | 20 (2) |
| Stool Frequency (#/day) | 1.6 (0.1) | 1.4 (0.1) | 2.7 (0.2) |
| Stool Consistency | 2.0 (0.1) | 1.9 (0.1) | 1.7 (0.1) |
| *4 months* | | | |
| | 98 | 107 | 103 |
| Feedings (#/day) | 5.9 (0.1) | 6.0 (0.1) | 6.6 (0.2) |
| Intake (mL/day) | 987 (33) | 926 (17) | ND |
| Spit-up (% of feedings) | 22 (2) | 18 (2) | 20 (2) |

TABLE IX-continued

| INTAKE SAND TOLERANCE Mean (SEM)[1] | | | |
|---|---|---|---|
| | NUC | CON | HM |
| Stool Frequency (#/day) | 1.4 (0.1) | 1.4 (0.1) | 1.5 (0.1) |
| Stool Consistency[2] | 2.0 (0.1) | 2.1 (0.1) | 2.1 (0.1) |

[1]Values in the same row with different superscripts are significantly different; $p < 0.05$.
[2]Mean rank consistency, where 1 = watery, 2 = mushy, 3 = soft, 4 = formed, 5 = hard.

The differential white counts and lymphocyte subset numbers of all infants receiving the formula according to this invention were well within normal ranges throughout the first year of life.

The vaccine response in this study was intended to be an immunological probe or indicator as to the responsiveness of the immune system in general. On the humoral side, tetanus toxoid vaccine was selected because it is a strong antigen, diphtheria toxoid was selected as a vaccine containing a weaker antigen, and Hib vaccine was selected as a very weak antigen that requires conjugation to a carrier protein to achieve a T-cell dependent immune response to the Hib polysaccharide component of the vaccine to be effective. It was thought that if nutritional intervention could evoke a difference in response that could be measured, that difference would more likely occur with the weaker antigens. While all infants would be expected to respond well to a strong antigen, like tetanus toxoid, a less vigorous response would be expected to a weak antigen. The Lederle Hib TITER® was selected specifically because the literature indicated that infants responded rather weakly after the first and second immunizations. Furthermore, the protein used as the conjugate in this vaccine, the CRM 197 protein (a non-toxic mutant diphtheria toxin), is antigenically very similar to diphtheria toxoid. Diphtheria toxoid vaccination also represents a response to a moderately weak antigen and correlates with immune response to the H. influenzae conjugate vaccine with the CRM 197 protein carrier.

The vaccine response at 6 months is taken from blood drawn immediately before the 6-month vaccination and represents the response 2 months after the second immunization given at 4 months of age. Already at that time point the Hib response was significantly higher in NUC than HM for both anti-Hib IgG and Hib Farr antibody. At 7 months, one month after the third immunization, NUC is significantly higher than CON and HM for Hib Farr. Hib IgG is higher at 7 months, and although there are not pairwise differences, the NUC group is double CON and HM (1.25 vs 0.63 and 0.60, respectively). The Hib Farr value was still significantly higher for NUCs at 12 months. For this weak antigen, a difference was first seen at 6 months. The difference became stronger at 7 months when the maximum response was expected and was maintained through 12 months of age.

In response to the moderately weak antigen diphtheria vaccine, there were no differences at 6 months, but at 7 months the NUC group was significantly higher than HM. By 12 months this difference was no longer present. For the moderately weak antigen, the direction of the present difference was the same as with the weak antigen (Hib) but was different only at the point of highest response.

For the strong antigen, tetanus, there were no differences among feeding groups at any time point.

These data strongly support the instant invention of specific nucleotide equivalents at specific levels and ratios to enhance the immune system. In this example and in commercial production of enteral formulas according to the invention, background levels of nucleotide equivalents are determined and then the formula would be supplemented with appropriate commodities, such as CMP, AMP, UMP and GMP, to the claimed levels and ratios. It should be remembered that by nucleotide equivalents is meant ribo-nucleotides, ribo-nucleosides, RNA, and ribo-nucleotide adjuncts, such as activated sugars. The sum of all these elements determine the total potentially available ribonucleotides equivalents.

Two additional pieces of data strongly support that the formula according to this invention provides an unexpected result. The number of subjects who have achieved protective levels of anti-Hib immunoglobulin as shown in Table VII is consistently 10% higher in the NUC group. The three-way comparison does not show a statistical difference. However, a two-way comparison between the NUC and CON formula groups at 7 months is significant (P<0.05).

An additional piece of data comes from two of the clinical sites which chose to collect morbidity data. As part of the study the incidence of diarrhea was determined at the two clinical study sites. Of 26 infants fed the NUC formula, only two reported diarrhea while 10 of 29 reported diarrhea in the CON formula. The $X^2$ analysis comparing the incidence of diarrhea in infants fed the two formulas is significant (P<0.05). In summary, the improved response to vaccination, the higher percent of subjects who have protective levels of antibodies, and the reduced incidence of diarrhea show that infants consuming the nucleotide-fortified formula according to this invention achieve enhanced immunological development as compared to those consuming the control formula.

INDUSTRIAL APPLICABILITY

The results from these experiments demonstrate that the enteral formula of this invention is effective in enhancing the immune system and treating diarrhea. The medical community is constantly searching for nutritional formulas that will benefit the infant. The present invention can clearly fill that need. The nucleotide equivalent level of the formula in the study is about the minimum for efficacious effect. Additionally, the formula is nutritionally complete as an infant formula. The manufacture of the formula utilizes conventional equipment and may be readily accomplished.

While the infant formula and method of making said formula herein described constitute a preferred embodiment of this invention, it is to be understood that the invention is not limited to this precise formulation or method and that changes may be made therein without departing from the scope of the invention which is defined in the appended claims.

What is claimed is:

1. An enteral formula, said formula comprising:
  1) protein, said protein being of a concentration of between 10 and 35 grams per liter of formula;
  2) fat, said fat being of a concentration of between 20 and 45 grams per liter of formula;
  3) carbohydrates, said carbohydrates being of a concentration of between 60 and 110 grams per liter of formula; and
  4) at least 70 mg of nucleotide equivalents per liter of formula, and wherein said nucleotide equivalents are nucleotide equivalents of each of adenosine, cytidine, guanosine and uridine; and wherein the weight ratio of CMP:UMP is from about 1.5:1 to about 2.6:1; of CMP:AMP is from about 2:1 to about 3.9:1; and of CMP:GMP is from about 1.75:1 to about 2.8:1.

2. An enteral formula according to claim 1 wherein the source of protein is selected from the group consisting of condensed skim milk, non-fat milk, acid whey, milk protein concentrate, nucleotide equivalent reduced soy protein and cheese whey.

3. An enteral formula according to claim 1 wherein said protein is of a concentration of between 13 and 20 grams per liter of formula and consists of 50–70% by weight condensed skim milk and 30–50% by weight cheese whey.

4. An enteral formula according to claim 1 wherein said fat is selected from the group consisting of soy oil, coconut oil, corn oil, safflower oils, fish oils, egg yolk oils, sunflower oils, microbial oils, fungal oils and blends thereof.

5. An enteral formula according to claim 4 wherein said fat is of a concentration of between 24 and 38 grams per liter of formula and consists of a blend of high oleic safflower oil, soy oil and coconut oil.

6. An enteral formula according to claim 1 which additionally comprises an antioxidant system, said antioxidant system consisting of R,R,R, α-tocopherol at a concentration of 10 to 30 IU per liter of formula, β-carotene at a concentration of 375 to 575 µg per liter of formula and selenium at a concentration of 14 to 32 mcg per liter of formula.

7. An enteral formula according to claim 1 wherein said nucleotide equivalents are present in the following ranges per liter of formula: CMP 29–39 mg; UMP 15–20 mg; AMP 10–15 mg and GMP 14–20 mg.

8. An enteral formula according to claim 1 wherein said protein is of a concentration of between 13 and 16 grams per liter of formula, said fat is a blend of soy oil, high oleic safflower oil and coconut oil and said carbohydrate is of a concentration of between 65 and 85 grams per liter of formula and consists of lactose.

9. An infant formula, said formula comprising:
  1) protein, said protein being of a concentration of between 10 and 35 grams per liter of formula;
  2) fat, said fat being of a concentration of between 20 and 45 grams per liter of formula;
  3) carbohydrates, said carbohydrates including those from total dietary fiber being of a concentration of between 60 and 110 grams per liter of formula; and
  4) at least 70 mg of nucleotide equivalents per liter of formula and said nucleotide equivalents are selected from the group consisting of RNA; mono-, di- and triphosphate esters of adenosine, cytidine, guanosine and uridine; and wherein the weight ratio of said cytidine nucleotide equivalents to said uridine nucleotide equivalents is from about 1.5:1 to about 2.6:1; of said cytidine nucleotide equivalents to said adenosine nucleotide equivalents is from about 2:1 to about 3.9:1; and of cytidine nucleotide equivalents to said guanosine equivalents is from about 1.75:1 to about 2.8:1.

10. A method of improving the immune response sensitivity of the immune system of a human, wherein said method comprises feeding a human in need of treatment a formula, the improvement comprising feeding said human a formula consisting essentially of:
  1) protein, said protein being of a concentration of between 10 and 35 grams per liter of formula;
  2) fat, said fat being of a concentration of between 20 and 45 grams per liter of formula;
  3) carbohydrates, said carbohydrates being of a concentration of between 60 and 110 grams per liter of formula; and 4) at least 70 mg of nucleotide equivalents per liter of formula, and wherein said nucleotide equivalents are nucleotide equivalents of each of adenosine, cytidine, guanosine and uridine; and wherein the weight ratio of CMP:UMP is from about 1.5:1 to about 2.6:1; of CMP:AMP is from about 2:1 to about 3.9:1; and of CMP:GMP is from about 1.75:1 to about 2.8:1.

11. A method according to claim 10 wherein the source of said protein is supplied in a form selected from the group consisting of condensed skim milk, non-fat milk, cheese whey, milk protein concentrate, nucleotide reduced vegetable protein, protein hydrolyzates and mixtures thereof.

12. A method according to claim 10 wherein said protein is of a concentration of between 13 and 20 grams per liter of formula and consists of 50–70% by weight condensed skim milk and 30–50% by weight cheese whey.

13. A method according to claim 10 wherein said fat is supplied in a form selected from the group consisting of soy oil, coconut oil, corn oil, safflower oils, fish oils, egg yolk oils, sunflower oils, fungal oils and blends thereof.

14. A method according to claim 10 wherein said fat is of a concentration of between 24 and 38 grams per liter of formula and consists of a blend of high oleic safflower oil, soy oil and coconut oil.

15. A method according to claim 10 which said protein is of a concentration of 13 to 15 grams per liter of formula, said fat is of a concentration of 30 to 40 grams per liter of formula and has as its source a blend of soy oils, coconut oils and high oleic safflower oil, and said carbohydrates are of a concentration of 70 to 80 grams per liter of formula, and dietary fiber, said dietary fiber is soy polysaccharide derived from soy beans.

16. A method according to claim 10 wherein said nucleotide equivalents are in the form of CMP, AMP, GMP and UMP, and are present at a level of up to 1.0 gram per liter of formula.

17. A method according to claim 10 wherein the formula additionally contains 10 to 30 IU of R,R,R, α-tocophenol per liter of formula, 400–575 µg of β-carotene per liter of formula and 14–32 mcg of selenium per liter of formula.

18. A method according to claim 10 wherein said nucleotide equivalents are present in the following ranges per liter of formula as fed: cytosine equivalents 30–33 mg; uridine equivalents 16–19 mg; adenosine equivalents 11–14 mg and guanosine equivalents 15–18 mg.

19. A method of improving the immune response sensitivity of the immune system of a human infant, said method comprising feeding a human infant in need of treatment a nutritional formula, the improvement comprising feeding a human infant a nutritionally complete formula comprising:
1) protein;
2) fat;
3) carbohydrates; and
4) at least 70 mg nucleotide equivalents per liter of formula, said nucleotides comprising the monophosphate esters of adenosine, cytidine, guanosine and uridine and wherein the weight ratio of CMP:UMP is from about 1.5:1 to about 2.6:1; of CMP:AMP is from about 2:1 to about 3.9:1; and of CMP:GMP is from about 1.75:1 to about 2.8:1.

20. A method according to claim 19 wherein said monophosphate esters are present in the following ranges per liter of formula as fed: CMP 30–33 mg; UMP 16–19 mg; AMP 11–14 mg and GMP 15–18 mg.

21. A method according to claim 19 wherein said protein is of a concentration of between 13 and 16 grams per liter of formula, said fat is a blend of soy oil, high oleic safflower oil and coconut oil, and said carbohydrate is of a concentration of between 65 and 85 grams per liter of formula and consists of lactose.

22. A method according to claim 19 wherein the formula additionally contains 10 to 30 IU of R,R,R, α-tocophenol per liter of formula, 400–500 µg of β-carotene per liter of formula and 14–32 mcg of selenate per liter of formula.

23. A method of improving the immune response sensitivity of the immune system of a human infant to an antigen, said method comprising feeding a human infant in need of treatment a nutritional formula, the improvement comprising feeding said human infant an infant formula that contains: 29–39 mg of CMP per liter of formula; 15–21 mg of UMP per liter of formula; 10–16 mg of AMP per liter of formula and 14–20 mg of GMP per liter of formula or their nucleotide equivalents and wherein the weight ratio of CMP:UMP is from about 1.5:1 to about 2.6:1; of CMP:AMP is from about 2:1 to about 3.9:1; and of CMP:GMP is from about 1.75:1 to about 2.8:1.

24. The method according to claim 23 wherein said human infant formula comprises per liter of formula:

CMP, 30–33 mg
UMP, 16–19 mg
AMP, 11–14 mg
GMP, 15–18 mg.

25. An enteral formula comprising per 100 Kcal of formula:
a) from about 1.5 to about 5 grams of protein;
b) from about 3 to about 6.5 grams of fat;
c) from about 8.7 to about 16 grams of carbohydrate; and
d) about 10 milligrams of nucleotide equivalents, wherein the nucleotide equivalents are nucleotide equivalents of adenosine, cytidine, guanosine and uridine and wherein the weight ratio of CMP:UMP is greater than about 1.5:1, the weight ratio of CMP:AMP is greater than about 2:1 and the weight ratio of CMP:GMP is greater than about 1.75:1.

26. An enteral formula comprising per 100 Kcal of formula:
a) from about 1.5 to about 5 grams of protein;
b) from about 3 to about 6.5 grams of fat;
c) from about 8.7 to about 16 grams of carbohydrate; and
d) nucleotide equivalents of adenosine, cytidine, guanosine and uridine and wherein the weight ratio of CMP:UMP is greater than about 1.5:1, the weight ratio of CMP:AMP is greater than about 2:1 and the weight ratio of CMP:GMP is greater than about 1.75:1.

27. An enteral formula according to claim 26, wherein the weight ratio of CMP:UMP is from about 1.5:1 to about 2.6:1: the weight ratio of CMP:AMP is from about 2:1 to about 3.9:1; and the weight ratio of CMP:GMP is from about 1.75:1 to about 2.8:1; and wherein at least some of the nucleotide equivalents are added as nucleotide monophosphates.

28. A nutritionally complete infant formula comprising: protein; fat; carbohydrate; and nucleotide equivalents of adenosine, cytidine, guanosine and uridine, wherein the weight ratio of CMP:UMP is greater than about 1.5:1, the weight ratio of CMP:AMP is greater than about 2:1 and the weight ratio of CMP:GMP is greater than about 1.75: 1 and wherein the level of nucleotide equivalents is about 10 milligrams per 100 Kcal of formula.

29. An enteral formula comprising:
a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) from about 2 to about 7 mg of nucleotide equivalents per gram of protein, wherein the nucleotide equivalents are adenosine, cytidine, guanosine and uridine nucleotide equivalents and wherein the weight ratio of CMP:UMP is greater than about 1.5:1, the weight ratio of CMP:AMP is greater than about 2:1 and the weight ratio of CMP:GMP is greater than about 1.75:1 the weight.

30. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) from about 1.5 to about 3.5 mg of nucleotide equivalents per gram of fat, wherein the nucleotide equivalents are adenosine, cytidine, guanosine and uridine nucleotide equivalents and wherein the weight ratio of CMP:UMP is greater than about 1.5:1, the weight ratio of CMP:AMP is greater than about 2:1 and the weight ratio of CMP:GMP is greater than about 1.75:1.

31. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) from about 0.6 to about 1.2 mg of nucleotide equivalents per gram of carbohydrate, wherein the nucleotide equivalents are adenosine, cytidine, guanosine and uridine nucleotide equivalents and wherein the weight ratio of CMP:UMP is greater than about 1.5:1, the weight ratio of CMP:AMP is greater than about 2:1 and the weight ratio of CMP:GMP is greater than about 1.75:1.

32. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) nucleotide equivalents of adenosine, cytidine, guanosine and uridine, wherein the level of cytidine equivalent is from about 0.8 to about 4 mg of CMP per gram of protein and wherein the weight ratio of CMP:UMP is greater than about 1.5:1, the weight ratio of CMP:AMP is greater than about 2:1 and the weight ratio of CMP:GMP is greater than about 1.75:1.

33. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) nucleotide equivalents of adenosine, cytidine, guanosine and uridine, wherein the level of cytidine equivalent is from about 0.6 to about 1.9 mg of CMP per gram of fat and wherein the weight ratio of CMP:UMP is greater than about 1.5:1, the weight ratio of CMP:AMP is greater than about 2:1 and the weight ratio of CMP:GMP is greater than about 1.75:1.

34. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) nucleotide equivalents of adenosine, cytidine, guanosine and uridine, wherein the level of cytidine equivalent is from about 0.2 to about 0.7 mg of CMP per gram of carbohydrate and wherein the weight ratio of CMP:UMP is greater than about 1.5:1, the weight ratio of CMP:AMP is greater than about 2:1 and the weight ratio of CMP:GMP is greater than about 1.75:1.

35. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) nucleotide equivalents of adenosine, cytidine, guanosine and uridine, wherein the level of cytidine equivalent is about 2 mg of CMP per 100 Kcal of formula and wherein the weight ratio of CMP:UMP is greater than about 1.5:1, the weight ratio of CMP:AMP is greater than about 2:1 and the weight ratio of CMP:GMP is greater than about 1.75:1.

36. An enteral formula comprising per 100 Kcal of formula:

a) from about 1.5 to about 5 grams of protein;

b) from about 3 to about 6.5 grams of fat;

c) from about 8.7 to about 16 grams of carbohydrate; and d) from about 1.5 to about 15 milligrams of nucleotide equivalents, wherein the nucleotide equivalents are nucleotide equivalents of adenosine, cytidine, guanosine and uridine and wherein the weight ratio of CMP:UMP is greater than about 1.5:1, the weight ratio of CMP:AMP is greater than about 2:1 and the weight ratio of CMP:GMP is greater than about 1.75:1.

37. An enteral formula according to claim 36, wherein the weight ratio of CMP:UMP is from about 1.5:1 to about 2.6:1; the weight ratio of CMP:AMP is from about 2:1 to about 3.9:1; and the weight ratio of CMP:GMP is from about 1.75:1 to about 2.8:1; and wherein at least some of the nucleotide equivalents are added as nucleotide monophosphates.

38. An enteral formula comprising:

a) from about 1.5 to about 5 grams of protein per 100 Kcal of formula;

b) from about 3 to about 6.5 grams of fat per 100 Kcal of formula;

c) from about 8.7 to about 16 grams of carbohydrate per 100 Kcal of formula; and d) nucleotide equivalents of adenosine, cytidine, guanosine and uridine, wherein the level of adenosine equivalent is about 1 mg of AMP per 100 Kcal of formula and wherein the weight ratio of CMP:UMP is greater than about 1.5:1, the weight ratio of CMP:AMP is greater than about 2:1 and the weight ratio of CMP:GMP is greater than about 1.75:1.

39. An enteral formula comprising:
a) from about 1.5 to about 5 grams of non-fat milk protein per 100 Kcal of formula;
b) from about 3 to about 6.5 grams of fat per 100 Kcal of formula;
c) from about 8.7 to about 16 grams of carbohydrate per 100 Kcal of formula; and
d) nucleotide equivalents of adenosine, cytidine, guanosine and uridine, wherein the level of cytidine equivalent is from about 0.8 to about 4 mg of CMP per gram of non-fat milk protein and wherein the weight ratio of CMP:UMP is greater than about 1.5:1, the weight ratio of CMP:AMP is greater than about 2:1 and the weight ratio of CMP:GMP is greater than about 1.75:1.

40. An enteral formula comprising per liter of formula:
a) from about 10 to about 35 grams of protein;
b) from about 20 to about 45 grams of fat;
c) from about 60 to about 110 grams of carbohydrate; and
d) about 40 milligrams of nucleotide equivalents, wherein the nucleotide equivalents are nucleotide equivalents of adenosine, cytidine, guanosine and uridine and wherein the weight ratio of CMP:UMP is greater than about 1.5:1, the weight ratio of CMP:AMP is greater than about 2:1 and the weight ratio of CMP:GMP is greater than about 1.75:1.

41. An enteral formula supplemented with nucleotide mono-phosphates, comprising per 100 Kcal of formula:
a) from about 1.5 to about 5 grams of protein;
b) from about 3 to about 6.5 grams of fat;
c) from about 8.7 to about 16 grams of carbohydrate; and
d) nucleotide equivalents of adenosine, cytidine, guanosine and uridine and wherein the weight ratio of CMP:UMP is from about 1.5:1 to about 2.6:1, the weight ratio of CMP:AMP is from about 2:1 to about 3.9:1, and the weight ratio of CMP:GMP is from about 1.75:1 to about 2.8:1.

42. An enteral formula supplemented with nucleotide mono-phosphates, comprising per 100 Kcal of formula:
a) from about 1.5 to about 5 grams of protein;
b) from about 3 to about 6.5 grams of fat;
c) from about 8.7 to about 16 grams of carbohydrate; and
d) from about 1.5 to about 15 milligrams of nucleotide equivalents, wherein the nucleotide equivalents are nucleotide equivalents of adenosine, cytidine, guanosine and uridine and wherein the weight ratio of CMP:UMP is from about 1.5:1 to about 2.6:1, the weight ratio of CMP:AMP is from about 2:1 to about 3.9:1, and the weight ratio of CMP:GMP is from about 1.75:1 to about 2.8:1.

* * * * *